United States Patent [19]
Pagan

[11] Patent Number: 5,915,383
[45] Date of Patent: Jun. 29, 1999

[54] CUFFED MEDICO-SURGICAL TUBES

[75] Inventor: Eric Pagan, Hythe, United Kingdom

[73] Assignee: Smiths Industries Public Limited Company, London, United Kingdom

[21] Appl. No.: 09/061,810

[22] Filed: Apr. 17, 1998

[30] Foreign Application Priority Data

Apr. 29, 1997 [GB] United Kingdom ............... 9708568

[51] Int. Cl.⁶ .................. A61M 16/00; A61M 29/00
[52] U.S. Cl. ............... 128/207.15; 128/911; 128/912; 128/DIG. 26; 600/115; 600/470; 604/41; 604/96; 606/191
[58] Field of Search ............ 128/207.15, 200.26, 128/911, 912, DIG. 26; 600/470, 115, 116; 604/41, 96, 101, 103, 104–109, 274, 278; 606/191, 192

[56] References Cited

U.S. PATENT DOCUMENTS

| | | |
|---|---|---|
| 3,866,599 | 2/1975 | Johnson . |
| 4,147,169 | 4/1979 | Taylor . |
| 4,641,653 | 2/1987 | Rockey .................................... 604/96 |
| 5,308,325 | 5/1994 | Quinn et al. ............................. 604/96 |
| 5,409,483 | 4/1995 | Campbell et al. ....................... 606/15 |
| 5,419,765 | 5/1995 | Weldon et al. .......................... 604/96 |
| 5,514,093 | 5/1996 | Ellis et al. .............................. 604/103 |
| 5,716,373 | 2/1998 | Wolvek et al. ......................... 606/194 |

FOREIGN PATENT DOCUMENTS

| | | | |
|---|---|---|---|
| 330376 | 8/1989 | European Pat. Off. .......... 128/207.15 |
| 95/32754 | 12/1995 | WIPO . | |

*Primary Examiner*—Kimberly L. Asher
*Attorney, Agent, or Firm*—Pollock, Vande Sande & Amernick

[57] ABSTRACT

The cuff on the patient end of a tracheal tube is attached at one end to the inside of the tube and at the opposite end to the outside of the tube. The cuff encloses an axial sleeve that is slidably mounted within the patient end of the tube and is urged forwardly by a resilient collar. The sleeve can be retracted by applying vacuum to the cuff and, when released, extends forwards to prevent the cuff occluding the patient end of the tube.

11 Claims, 7 Drawing Sheets

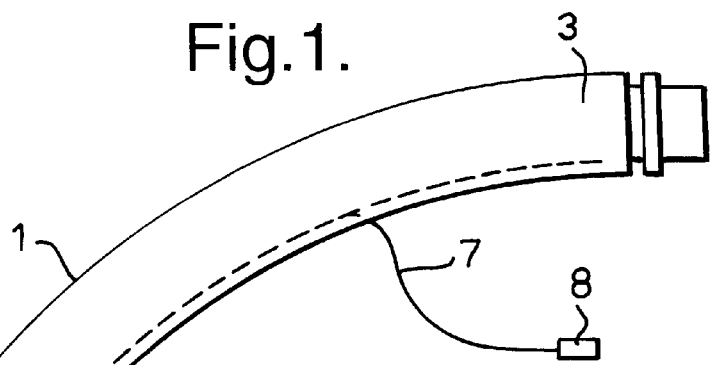
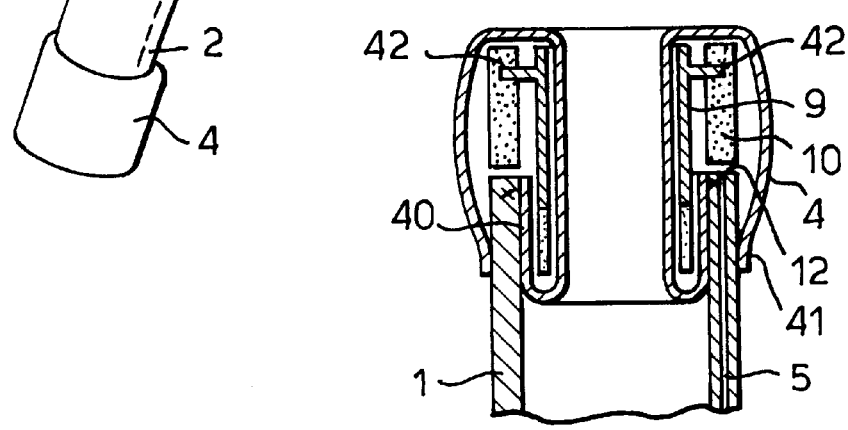
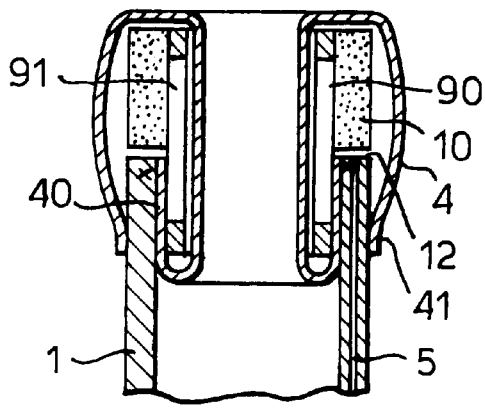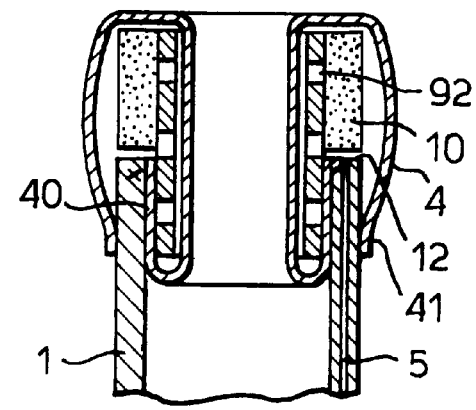

Fig.3.
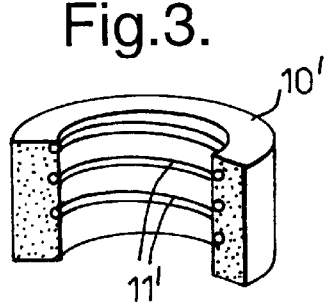
Fig.4. Fig.5. Fig.6. Fig.7.
 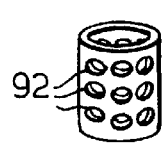 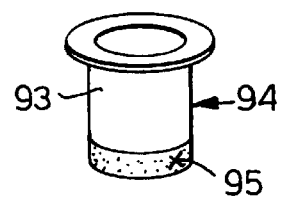 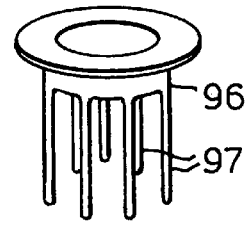

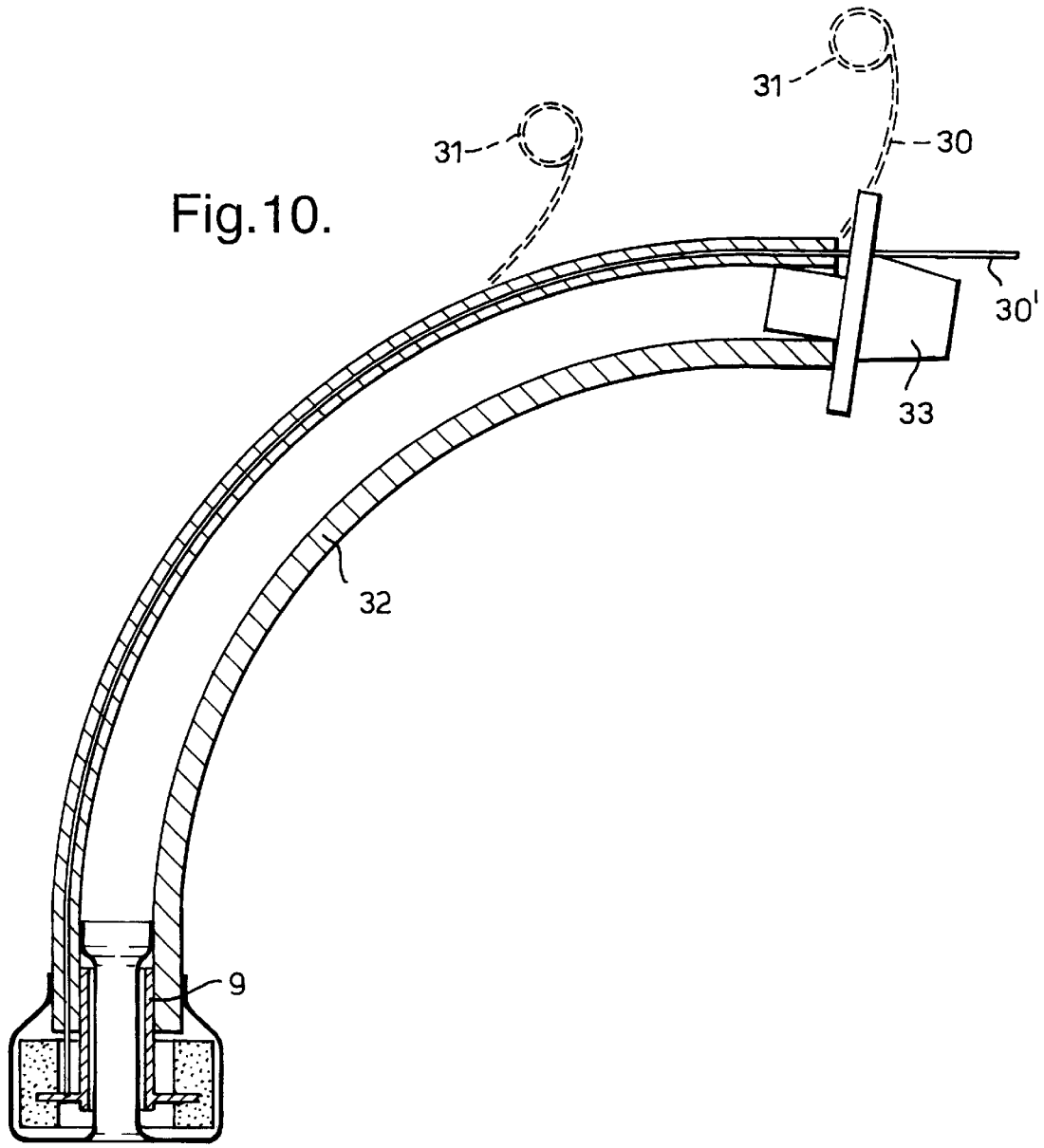

CUFFED MEDICO-SURGICAL TUBES

BACKGROUND OF THE INVENTION

This invention relates to cuffed medico-surgical tubes.

Various medico-surgical tubes have an inflatable cuff encircling the tube, which is used to make a seal with a part of the body in which the tube is inserted. The cuff is preferably located as close as possible to the tip of the tube shaft so that it is kept away from the surrounding tissue, to avoid trauma. Although it is possible for a tube to have a cuff that projects beyond the end of the shaft, this brings with it a risk that the cuff might occlude the opening of the shaft, because of the flexible nature of the cuff.

BRIEF SUMMARY OF THE INVENTION

It is an object of the present invention to provide an improved cuffed medico-surgical tube.

According to one aspect of the present invention there is provided a cuffed medico-surgical tube having a tubular shaft and an expansible cuff member mounted with the shaft close to its patient end, the cuff member projecting beyond the patient end of the shaft in its expanded state, the tube including an axial sleeve member mounted with the shaft close to said patient end, the sleeve member being slidable axially forwards beyond the patient end of said shaft, the cuff member and sleeve member being displaceable forwardly together, and the sleeve member being arranged to prevent the cuff member occluding the patient end of the shaft.

The sleeve member may extend within the bore of the shaft at its patient end. One end of the cuff is preferably attached to the inside of the shaft and the sleeve member is preferably enclosed within the cuff member. The sleeve member preferably has a resilient member attached therewith. The sleeve member may be perforated and may be retractable by vacuum applied to the cuff member. The tube may include an elongate member coupled at its patient end with the cuff member, the machine end of the elongate member projecting from the tube towards the machine end of the tube so that the cuff member can be displaced by manually manipulating the machine end of the elongate member. The elongate member may have a resilient portion towards its patient end. The tube is preferably a tracheal tube.

Examples of a cuffed endotracheal tube in accordance with the present invention, will now be described, by way of example, with reference to the accompanying drawings.

BRIEF DESCRIPTION OF THE DRAWINGS

FIG. 1 is a side elevation view of the tube;

FIG. 2 is an enlarged sectional side elevation view of the patient end of the tube with the cuff in an expanded state;

FIGS. 2a and 2b are enlarged sectional side elevation views of the patient end of two alternative tubes.

FIG. 3 is a cut-away perspective view of an alternative part for the tube;

FIGS. 4 and 5 are perspective views of parts of the tubes shown in FIGS. 2a and 2b, respectively;

FIGS. 6 and 7 are perspective views of other alternative parts for the tube;

FIG. 10 is a sectional side elevation view of a further alternative tube;

DETAILED DESCRIPTION OF THE PREFERRED EMBODIMENTS

Figure 8:
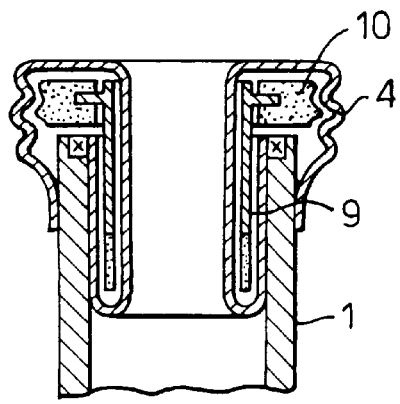
FIG. 8 is an enlarged sectional side elevation view of the patient end of the tube with the cuff in retracted state.

With reference to FIGS. 1 to 8, the endotracheal tube has a curved tubular shaft 1 with a hollow bore, a patient end 2 and a machine end 3. A cuff 4 encircles the shaft 1 at the patient end 2 and is expanded and deflated via a lumen 5 extending within the wall of the shaft and communicating with the inside of the cuff. Towards its rear end, the lumen 5 is connected with a small bore line 7, which extends to a connector 8. The tube also includes a slidable sleeve 9 located within the cuff 4.

The cuff 4 is of tubular shape and is attached at one end 40 to the inside of the shaft 1 and at the other end 41 to the outside of the shaft. The sleeve 9 is of cylindrical shape and extends coaxially within the patient end of the shaft. The inside end 40 of the cuff 4 is folded around the rear end of the sleeve 9 and extends along the inside of the sleeve, around its forward end and rearwardly back along its outside to a point along the outside of the shaft where it is attached to its wall, so that the sleeve is enclosed within the cuff. The cuff 4 traps within it a resilient collar 10, which encompasses the forward end of the sleeve 9, the rear end of the collar being attached to the forward end of the shaft 1 and the collar being attached with the sleeve close to its forward end by means of an outwardly projecting rib 42. The collar 10 may be of a resilient foam or a bundle of loose resilient fibres, or it may be provided by a one or more springs. Alternatively, the collar 10' may be of a foam or similar resilient material with additional reinforcing elements 11', as shown in FIG. 3, extending diagonally, helically or radially. The reinforcing elements 11' may be embedded, injection moulded, bonded or welded to the resilient material.

The sleeve 9 may be a simple cylindrical sleeve. Alternatively, the sleeve 90 may be perforated with axially-extending slots 91, as shown in FIGS. 2a and 4, or circular holes 92, as shown in FIGS. 2b and 5. Alternatively, the sleeve 93 could have a rigid forward end 94 and a soft rear end 95, as shown in FIG. 6, so as to reduce risk of damage to the cuff 4 where it is wrapped around the rear end of the sleeve. In another arrangement, as shown in FIG. 7, the sleeve 96 comprises a cylindrical array of parallel pins 97.

The lumen 5 through the shaft 1 opens into the space within the cuff 4 through an opening 12. In its natural state, as shown in FIG. 2, both the cuff 4 and the sleeve 9 project beyond the forward end of the shaft 1 so that the forward tip of the tube is cushioned right up to its edge, the cuff projecting radially outwardly to form a seal with the inside of the trachea.

The cuff 4 is compressed for intubation by applying a vacuum to the line 7, so that the cuff and the resilient collar 10 are compressed and retracted in the manner shown in FIG. 8. The tube is introduced in this state and, when located correctly, the vacuum is removed so that the resilience of the collar 10 can expand the cuff 4 forwardly and outwardly. If desired, a small amount of air could be introduced to expand the cuff 4 further outwardly. Any inadvertent overpressure will produce a forward extension of the cuff 4, rather than an inward extension, so there is no risk of the cuff occluding the end of the shaft 1.

Figure 9:
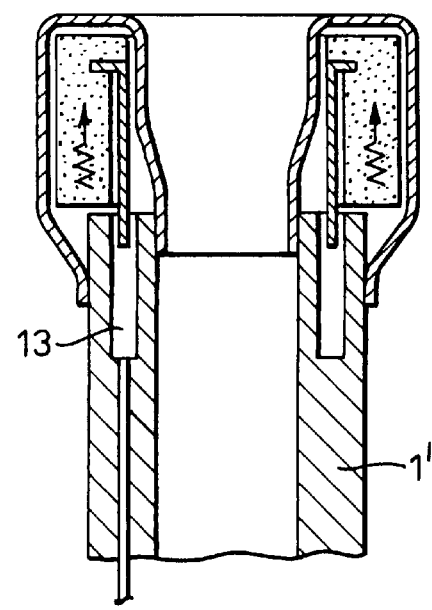
FIG. 9 is an enlarged sectional side elevation view of the patient end of a modified tube.

Various modifications are possible to the invention. For example, the sleeve 9 need not slide inside the end of the shaft but could, for example, slide in an annular channel 13 formed at the end of the shaft 1', as shown in FIG. 9.

Figure 11:
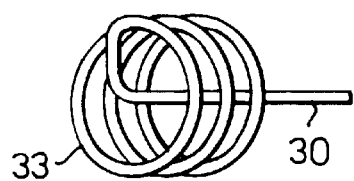
FIGS. 11 and 12 are perspective views of alternative parts for a tube.
Figure 12:
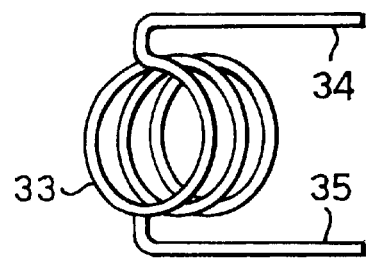
Figure 13:
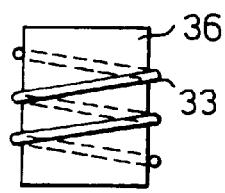
FIG. 13 is a side elevation view of a modified form of the part shown in FIG. 12.
Figure 14:
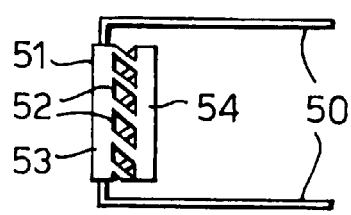
FIG. 14 is a side elevation view of a modification of the parts shown in FIGS. 11 to 13.
Figure 15:
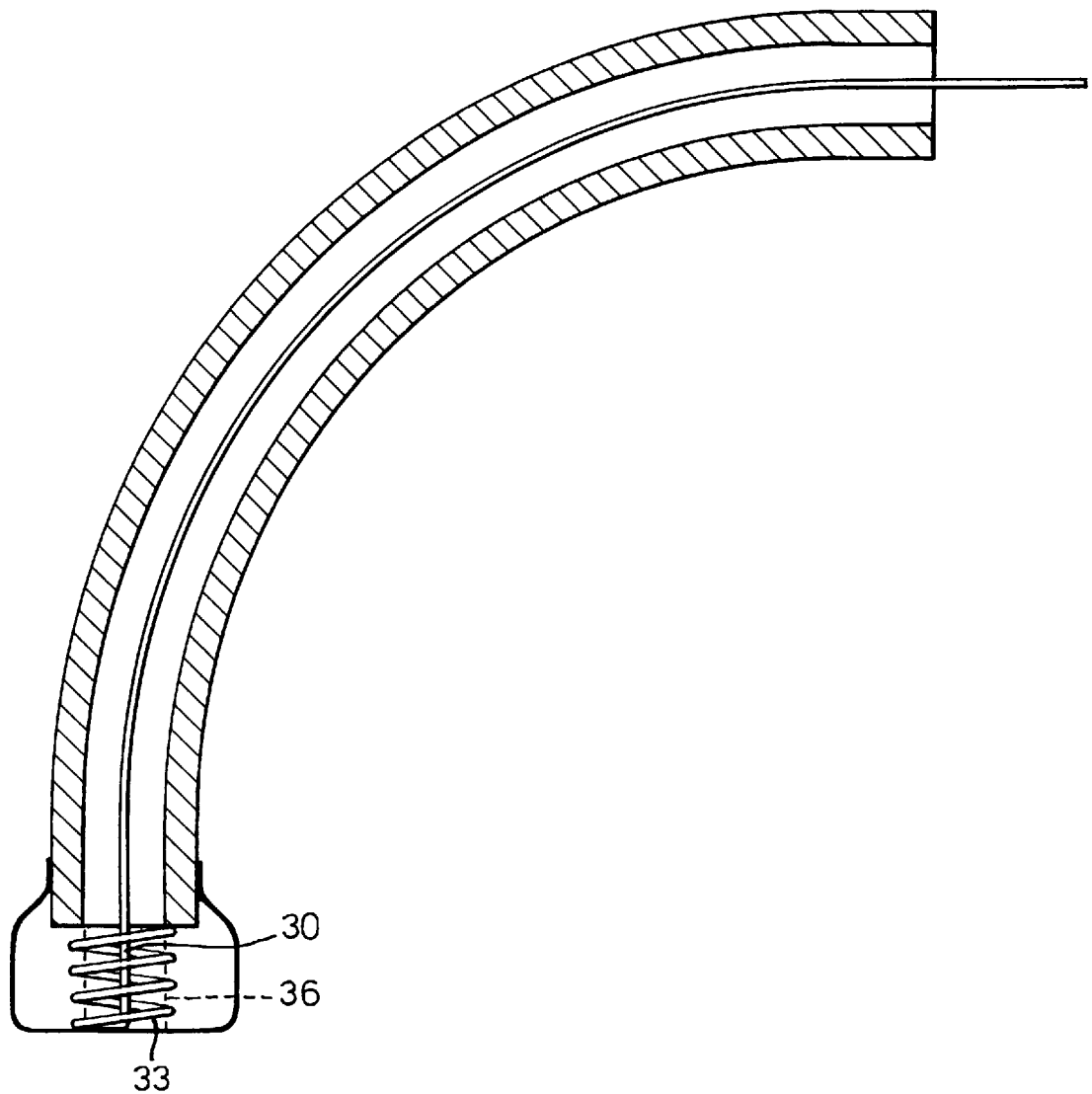
FIGS. 15 to 17 are sectional side elevation views of alternative tubes incorporating the parts shown in FIGS. 11, 12 and 14, respectively.
Figure 16:
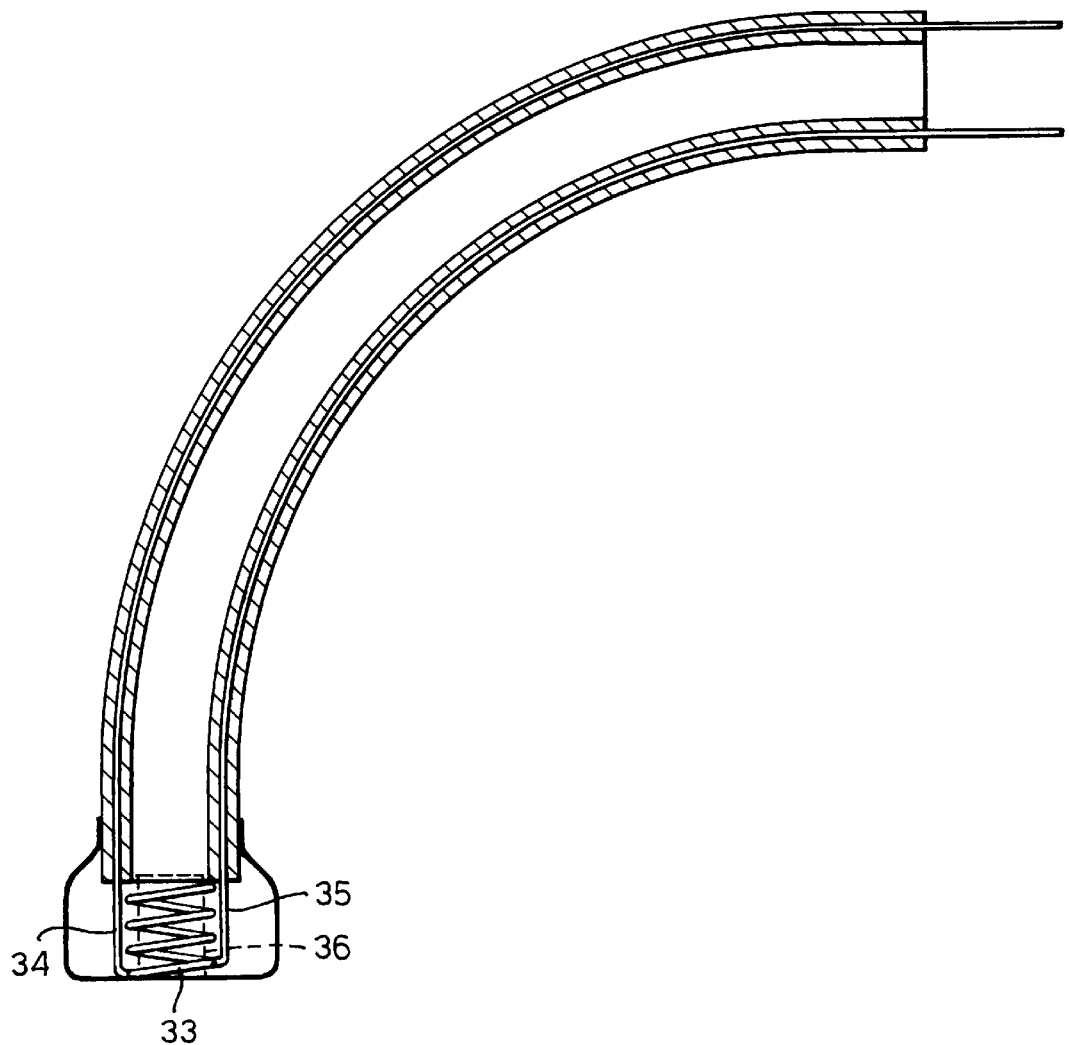
Figure 17:
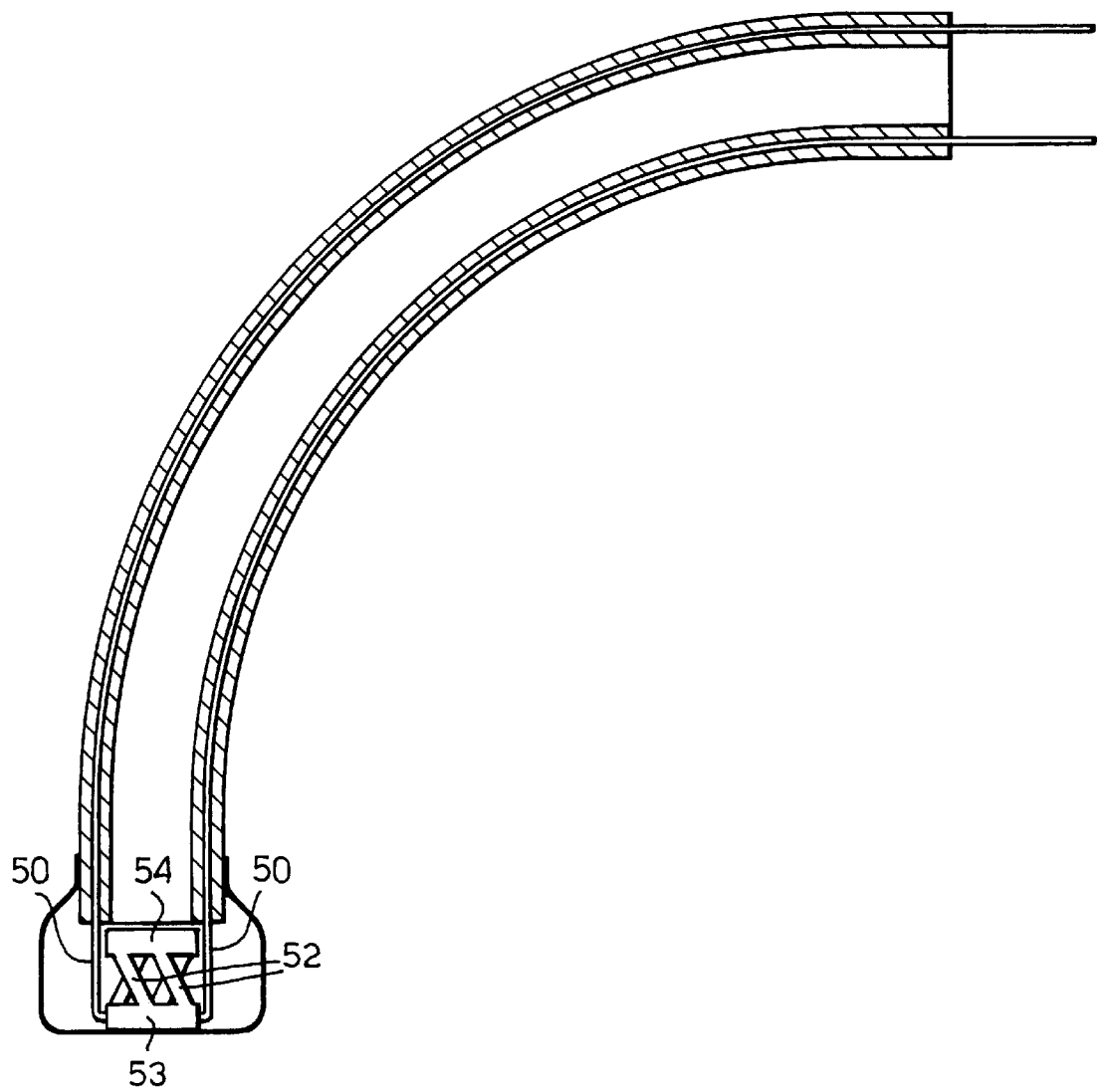

Instead of using a resilient member to expand the cuff, the tube could have an elongate member such as a wire 30 slidable along a passage in the wall of the shaft 32 and attached at its forward end to the sleeve 9 and at its rear end to a handle 31, as shown in FIG. 10. The wire could alternatively extend along the main bore of the shaft. The wire could protrude from a machine end connector 33 on the shaft 32, as shown at 30', and be arranged such that the wire is pushed forwards to expand the cuff 4 by contact with a part of a mating connector.

Where a wire is used, it may not be necessary to use a collar of a resilient material since the wire 30 itself could be formed with a resilient portion such as by coiling it into a helix 33 at its patient end, as shown in FIGS. 11 and 15. Two wires 34 and 35 could be used attached to opposite sides of the helix 33, as shown in FIGS. 12 and 16. The helix 30 could be attached to a flexible tubular element 36 to limit the extent of its axial extension, as shown in FIG. 13. In another arrangement, the wires 50 could be attached to a tubular basket assembly 51 with diagonal struts 52 extending between two end pieces 53 and 54, as shown in FIGS. 14 and 17.

The present invention is not confined to tracheal tubes but could be used in any cuffed medico-surgical tube, such as oropharyngeal tubes or laryngeal masks. The extensible axial sleeve member could be provided by a part of the cuff member, such as a part reinforced, such as by braiding.

What I claim is:

1. A cuffed medico-surgical tube comprising: a tubular shaft having a bore, a patient end and a machine end; an expansible cuff member mounted with said shaft close to said patient end; and an axial sleeve member, wherein said cuff member projects beyond the patient end of said shaft in an expanded state, wherein said axial sleeve member is mounted with said shaft close to said patient end, wherein said sleeve member is slidable axially forwards beyond the patient end of said shaft, said cuff member and said sleeve member being displaceable forwardly together, and wherein the said sleeve member is arranged to prevent the said cuff member occluding the said patient end of said shaft.

2. A tube according to claim 1, wherein said sleeve member extends within the bore of said shaft at the patient end of said shaft.

3. A tube according to claim 1, wherein one end of said cuff member is attached to an inside of said shaft.

4. A tube according to claim 1, wherein the said sleeve member is enclosed within said cuff member.

5. A tube according to claim 1, wherein said sleeve member has a resilient member attached therewith.

6. A tube according to claim 1, wherein said sleeve member is perforated.

7. A tube according to claim 1, wherein the tube includes a lumen by which vacuum can be applied to said cuff member to retract said sleeve member.

8. A tube according to claim 1, wherein said tube includes an elongate member having a patient end and a machine end, wherein said elongate member is coupled at its patient end with said cuff member, and wherein the machine end of said elongate member projects from said tube towards the machine end of said tube so that the said cuff member can be displaced by manually manipulating the machine end of said elongate member.

9. A tube according to claim 8, wherein said elongate member has a resilient portion towards its patient end.

10. A cuffed tracheal tube comprising: a tubular shaft having a bore, a patient end and a machine end; an expansible cuff member mounted with said shaft close to said patient end; and an axial sleeve member, wherein said cuff member projects beyond the patient end of said shaft in an expanded state, wherein said axial sleeve member is slidably mounted within the patient end of said shaft, wherein one end of said cuff member is attached with an inside of said shaft and another end of said cuff member is attached with an outside surface of said shaft so as to enclose said sleeve member, said cuff member and said sleeve member being displaceable forwardly together so that a part of said sleeve member projects beyond the end of said shaft and prevents the said cuff member occluding the patient end of said shaft.

11. A cuffed tracheal tube comprising: a tubular shaft having a bore, a patient end and a machine end; an expansible cuff member mounted with said shaft close to said patient end; an axial sleeve member; and a resilient member engaging said sleeve member and said shaft, wherein said cuff member projects beyond the patient end of said shaft in an expanded state, wherein said axial sleeve member is slidably mounted within the patient end of said shaft, wherein one end of said cuff member is attached with an inside of said shaft and another end of said cuff member is attached with an outside surface of said shaft so as to enclose said sleeve member, said cuff member and said sleeve member being displaceable forwardly together by said resilient member so that a part of said sleeve member projects beyond the end of said shaft and prevents the said cuff member occluding the said patient end of said shaft.

* * * * *